United States Patent [19]

Sievers

[11] Patent Number: 5,009,664
[45] Date of Patent: Apr. 23, 1991

[54] MARROW NAIL FOR THE TREATMENT OF BONE FRACTURES

[75] Inventor: Uve Sievers, Ludwigshafen, Fed. Rep. of Germany

[73] Assignee: Mecron Medizinische Produkte GmbH, Berlin, Fed. Rep. of Germany

[21] Appl. No.: 254,086

[22] Filed: Oct. 6, 1988

[30] Foreign Application Priority Data

Oct. 6, 1987 [DE] Fed. Rep. of Germany ....... 3734108

[51] Int. Cl.$^5$ .......................... A61F 2/28; A61F 5/04
[52] U.S. Cl. ......................................... 623/16; 606/62
[58] Field of Search ....................... 623/16, 20, 22, 23; 128/92 YK, 92.42

[56] References Cited

U.S. PATENT DOCUMENTS

| 2,537,070 | 1/1951 | Longfellow | 128/92.42 |
| 2,602,445 | 7/1952 | Gallant et al. | 128/92 Y K |
| 3,893,196 | 7/1975 | Huchman | 128/92.42 |
| 3,977,398 | 8/1976 | Burstein | 128/92.42 |
| 4,446,857 | 5/1984 | Otte et al. | 128/92.42 |
| 4,459,708 | 7/1984 | Buttazzeni | 123/23 |
| 4,522,202 | 6/1985 | Otte et al. | 128/92.42 |
| 4,662,887 | 5/1987 | Turner | |

FOREIGN PATENT DOCUMENTS 913228 6/1954 Fed. Rep. of Germany ... 128/92.42

OTHER PUBLICATIONS

"Die Bundel-Nagelung" (Bundle Nailing) Published by Springer-Verlag, Berlin, Gottingen, Heidelberg, 1961, pp. 3-26 and 56-58.
Hansjürgen Saechtling, Kunststoff Taschenbuch 23rd Edition, Carl Hanser Verlag, Munich, 1986 pp. 1, 316.

*Primary Examiner*—David J. Isabella
*Attorney, Agent, or Firm*—Spencer & Frank

[57] ABSTRACT

A marrow nail for use in a marrow cavity nailing procedure for the treatment of bone fractures, including a tubular, carbon fiber reinforced plastic nail body having a tip which has a distal end, the nail body being elongated and being curved along its length, and the tip having a conically tapered outer surface which is ground and which tapers toward the distal end.

12 Claims, 2 Drawing Sheets

MARROW NAIL FOR THE TREATMENT OF BONE FRACTURES

CROSS REFERENCE TO RELATED APPLICATIONS

The subject matter of this application is related to that contained in copending U.S. Pat. application No. 07/254,180 to Curt Kranz and Uve Sievers, entitled "MARROW NAIL FOR THE TREATMENT OF BONE FRACTURES ACCORDING TO THE MARROW CAVITY NAILING PROCEDURE AND MARROW NAIL TOOL", filed on Oct. 6, 1989 concurrently with the present application.

BACKGROUND OF THE INVENTION

The present invention relates to a marrow nail for the treatment of bone fractures according to a marrow cavity nailing procedure.

Marrow nailing methods are known, for example, the publication entitled "Die Bündel-Nagelung" [Bundle Nailing] published by Springer-Verlag, Berlin, Göttingen, Heidelberg, 1961, pages 3-26 and 56-58, discloses the treatment of fractures in long tubular bones by a marrow nailing method in which a metallic marrow nail is driven through the marrow cavity of a selected bone across the location of the fracture, and is there anchored in the marrow cavity to stabilize the fracture after the bone has been appropriately repositioned. After complete healing of the fracture, the marrow nail is then removed. The desired stabilization of a fracture in such a marrow nailing procedure is realized by clamping the marrow nail in either the transverse or longitudinal direction, with the marrow nail having a variety of permissible cross-sectional configurations.

However, the known metal marrow nails have several drawbacks. The rigid metal nails used in the prior art involve the risk of splitting the bone, the risk of the nail tip being caught at an inappropriate location, the risk of the nail being bent, the risk of bending the nail during the nailing process due to the relatively weak resistance of the nails to bending stresses. Other types of marrow nailing, such as, for example, bundle nailing by means of a bundle of thin elastic steel nails, have the drawback that their stability is not always ensured and that certain treatments are necessarily employed in conjunction with each type of nail.

For the treatment of pertrochanteric and subtrochanteric fractures according to the marrow nailing procedure, it is also known to use so-called spring nails which are arranged in the marrow tube in an elastically clamped arrangement and are distributed in a fan shape at the end opposite the point where they are driven in. If there is pressure stress on a bone stabilized in this manner, such pressure is distributed to the bone uniformly over the entire length of the nails. The prior art spring nails provide good support in the proximal part of the fracture as well as good rotational stability. Due to the resiliency of these prior art spring nails, it is possible to employ turning of a preliminary driver to cause threading of the bone fragments and accurate repositioning of the fragments. As with the use of rigid marrow nails, spring nails must be made of a high quality metal to produce the required strength and elasticity characteristics and to avoid adversely affecting the bone tissue. Additionally, if spring nails are employed, it is the custom to employ three or more nails to fix pertrochanteric fractures.

The prior art bone nails have the drawback that they are bodies made of a foreign material with respect to the human body, so that it is necessary in every case to extract the prior art bone nails in a second surgical procedure. Moreover, since the characteristics of the prior art bone nails are not well adapted to conform to those of the surrounding bone material, relative movements between the bone material and the bone nails cause damaging results due to their different stress behavior when the bone is placed under load.

SUMMARY OF THE INVENTION

It is an object of the present invention to provide a bone nail which is made of a material that, in a usual case, may remain in a human body without undue risk of complications resulting therefrom.

It is another object of the invention to provide a bone nail which has material properties which behave similarly to the bone substance in which the bone nail is embedded, such that the bone nail is compatible with the bone in which it is embedded.

It is another object of the invention to provide bone nail which, after insertion in a first surgical procedure, can be further manipulated in a later surgical procedure if necessary, and used in conjunction with another endoprosthesis, and which can be manipulated or worked upon using conventional tools.

This is accomplished by the marrow nail according to the invention for use in a marrow cavity nailing procedure for the treatment of bone fractures, including:

a tubular, carbon fiber reinforced plastic nail body having a tip which has a distal end, the nail body being elongated and being curved along its length; and the tip having a conically tapered outer surface which is ground and which tapers toward the distal end.

The invention advantageously provides a substitute material for steel materials for use in osteosynthesis, the material employed having a relatively high load bearing capability, being relatively light-weight, and being capable of adapting to the deformation behavior of the surrounding bone material when under load so that the bond of the bone and the substitute material according to the invention constitutes a dynamic unit which will be maintained even under load.

It is a further advantage that during subsequent surgical procedures, such as may be necessary particularly in older patients or those having tumors, the endoprosthesis can remain at its original location and can be worked on in such a manner that an extension of the prosthesis can be provided, or other endoprosthesis components can be inserted, without a need to employ metal-working tools. The use of such metalworking tools would involve extensive damage to the surrounding tissue.

Moreover, the marrow nail according to the invention permits a bond to be formed with further endoprosthetic components, which can be established by subsequent working of the marrow nail involving, for example, the cutting of threads in the marrow nail. This subsequent working can be performed with simple bone working materials used for operating upon normal bone substance. Any chips created during the procedure of installing or removing the marrow nail according to the invention do not constitute a danger for the organism and no special care must be taken to remove such chips, in contrast to the situation where metal chips are produced as in the prior art.

It is another advantage that the nail according to the invention, which is a hollow body, need not be slotted in order to impart to it the elasticity required for driving it in, in contrast to a Küntscher nail, for example. By configuring the marrow nail according to the invention as a closed, cylindrical hollow body it is possible to obtain a marrow nail having the elasticity required for driving it in while also maintaining its torsional stiffness, in contrast to the Küntscher nail, where such torsional stiffness is considerably reduced due to the possibility that the two free edges can be longitudinally displaced in the region of the slot.

The marrow nail according to the invention exhibits a high resistance to bending, rotational stability, low material fatigue under load, and high elasticity when the nail is driven in so as to require relatively little driving force. The nail is relatively inexpensive and is relatively easy to manufacture. It is tissue compatible and is capable of reliably stabilizing the fragments of a fracture by use of just a single nail.

In an advantageous modification of the invention, the marrow nail has the cross section of a hollow cylinder and a sharply ground, annular cutting edge at its tip.

In a further advantageous modification, the marrow nail is composed of a tube knit of carbon fibers and a hardenable synthetic resin. The tube may contain carbon fibers which are arranged in a crisscross interconnection while the hardenable synthetic resin may be composed of a biocompatible TEEC matrix material in which the carbon fibers are embedded and which preferably hardens at a high temperature of approximately 380° C.

In a further advantageous embodiment, the marrow nail is bent in the shape of a C. In addition, the marrow nail according to the invention may include a metal force introduction element which is inserted during fabrication into the marrow nail head and which is composed, for example, of a hollow cylinder whose interior wall has a rough surface.

The invention will be described in greater detail below with reference to an embodiment that is illustrated in the drawings.

DETAILED DESCRIPTION OF THE PREFERRED EMBODIMENT

Figure 1:
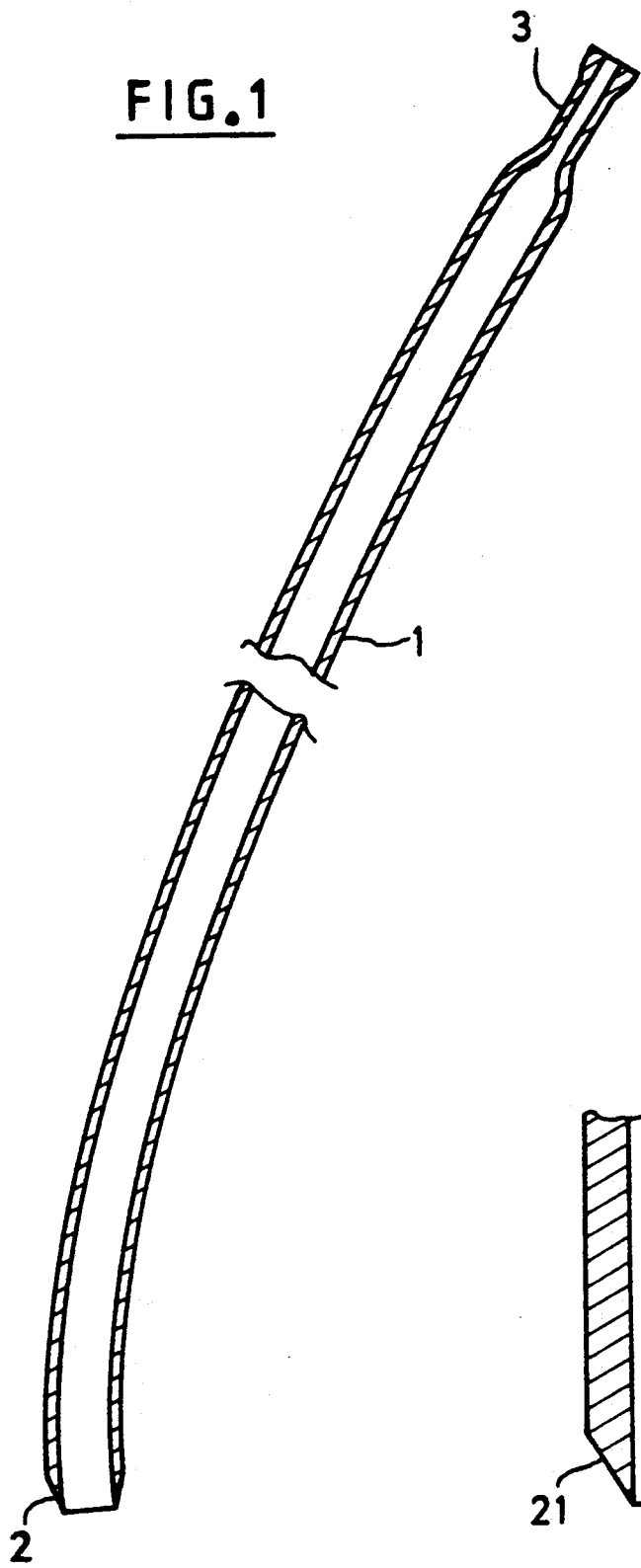
FIG. 1 is a longitudinal sectional view of a marrow nail according to the invention, composed of a carbon fiber reinforced plastic.

FIG. 1 is a longitudinal section taken through a tubular marrow nail 1 which is composed of carbon fiber reinforced plastic. As seen in FIG. 1, the marrow nail 1 is slightly curved longitudinally generally in the shape of a C, and has a tip 2 as well as a constricted head 3. In the region of the tip 2, the diameter of the marrow nail 1 is about 10 mm. Preferably, the tubular marrow nail 1 has the shape of a hollow cylinder.

The carbon fiber reinforced plastic marrow nail 1 is manufactured starting with a tube of carbon fiber which is preferably knit in a crisscross fashion having many interconnections. This tube is then saturated with a hardenable plastic. The hardenable plastic is preferably composed of a biocompatible PEEK (polyetherc-lkerketone, matrix material which embeds the carbon fibers and which hardens at a high temperature of preferably 380° C.

Alternatively, other materials can be used for the hardenable plastic, such as, for example, polyamide 6 or polyamide 6, 6. Additionally, materials can be used which are customarily referred to as bulk plastics, such as, for example, polyolefins (polyethylene, polypropylene). In conjunction with the carbon fibers according to the invention, this produces a high strength marrow cavity nail 1 which is distinguished by high tensile strength and stiffness as well as high heat resistance. These qualities are ordinarily associated only with metal materials; however, the aforementioned characteristics of the novel nail 1 can even exceed the corresponding characteristics of a similar nail made of a metal material.

The C or J shape of the marrow nail 1 can be obtained by the introduction of a suitable core in the form of, for example, a cylindrical wire having the corresponding outer diameter and around which the knit tube of carbon fibers is formed or drawn. After application and hardening of a suitable synthetic resin, the core (not shown) can be removed and the marrow nail 1 made of carbon fiber reinforced plastic can be worked further.

To obtain a smooth surface for the marrow nail 1, the hardenable synthetic resin can be applied under high pressure, or alternatively the surface of the marrow nail 1 may subsequently be polished.

The use of a carbon fiber reinforced plastic material for the production of a marrow nail 1, in conjunction with formation of a suitable diameter of the marrow nail 1, ensures that when the marrow nail 1 is driven into the marrow cavity of a bone, it is possible to guide the marrow nail 1 accurately from its point of entry in the bone without bending of the marrow nail 1 and without the marrow nail 1 having uncontrolled movements. The tip 2 of the marrow nail 1 has a sharply ground annular cutting edge which permits driving in of the marrow nail 1 with little force while avoiding crushing of bone marrow during the driving-in process.

When the marrow nail 1 is inserted in the bone, it is distinguished by its high rotational stability and its ability to absorb even the strongest vibrations without material fatigue. A further advantage is its good tissue compatibility and the avoidance of any negative influences on the bone marrow such as may occur, for example, in conjunction with a steel nail due to corrosion. The cylindrical, slightly bent shape of the marrow nail 1, in conjunction with its selected diameter, permits secure contact of the marrow nail 1 in the marrow cavity of the bone and thereby provides the prerequisite characteristics necessary for a marrow nail used for the stabilization of bone fragments, when only a single marrow nail is used.

Extraction of the marrow nail 1 when the fracture is healed can be performed easily by gripping the constricted or flattened head 3 of the marrow nail 1, without the danger of the marrow nail 1 breaking off, since the marrow nail 1 is composed of a fiber material which is bonded together, rather than metal which tends to break relatively easily.

Figure 2:
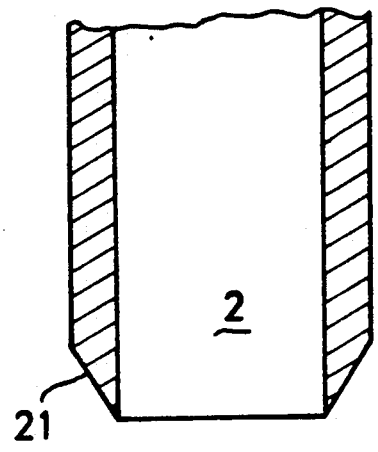
FIG. 2 is an enlarged sectional view of the tip of the marrow nail of FIG. 1.

FIG. 2 shows, at an enlarged scale, the tip 2 of the marrow nail 1 and clearly shows a conically, slightly tapered outer face 21 of the tip 2. This outer face 21 is created preferably by sharp grinding of the tip 2, so as to thereby create an annular cutting edge.

Figure 3:
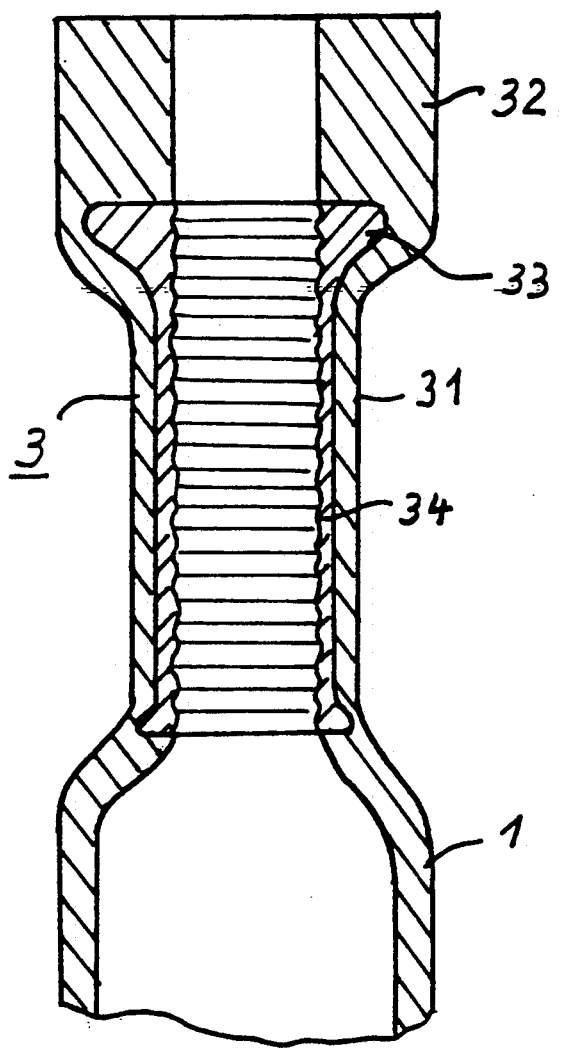
FIG. 3 is an enlarged sectional view of the marrow nail head of FIG. 1.

FIG. 3 shows, to an enlarged scale, the marrow head 3 which is composed of a cylindrically constricted or flattened portion 31 and an outwardly thickened, bent or crimped end piece 32, hereinafter referred to as relatively enlarged portion 32. A metal force introducing element 34 in the form of a hollow cylinder of titanium in this embodiment is inserted into the head 3 in the region of the constricted portion 31 before that portion is constricted to form its final shape, namely that of the cylindrically constricted or flattened portion 31. The interior surface of the force introducing element 33 is roughened, preferably in the form of parallel grooves or threaded grooves so that head 3, and with it the entire marrow nail 1, can be pulled out of the marrow cavity in which it has been inserted by the gripping thereof with a suitable tool, for example a forceps, in a force-locking manner for extraction of the marrow nail 1 from the marrow cavity or to change the position of the tip 2 of the nail 1 for repositioning of the marrow nail 1.

Additionally, the constricted or flattened head 3 of the hollow cylindrical marrow nail 1 can also facilitate the attachment of a suitable tool which is to be used for driving the marrow nail 1 into the marrow cavity of a bone.

The metal force introducing element 34 may be inserted, prior to formation of the final marrow nail 1, into the fabric of carbon fibers when the marrow nail 1 is being manufactured. The force introducing element 34 can therefore be bonded to the plastic used to coat the carbon fibers so that, during hardening of the plastic, a firm bond occurs between the plastic-and-carbon-fiber portion of the marrow nail head 3 with the metal force introducing element 34.

It will be understood that the above description of the present invention is susceptible to various modifications, changes, and adaptations, and the same are intended to be comprehended within the meaning and range of equivalents of the appended claims.

What is claimed is:

1. A marrow nail for use in a marrow cavity nailing procedure for the treatment of bone fractures, comprising:
   a tubular, carbon fiber reinforced plastic nail body having a tip, said tip having a distal end, said tip having a hollow circular cross-section and a conically tapered outer surface which tapers in a direction toward said distal end forming a sharp annular cutting edge.

2. A marrow nail as defined in claim 1, wherein said tubular, carbon fiber reinforced plastic nail body includes carbon fibers which are disposed in a knit arrangement having a tubular shape.

3. A marrow nail as defined in claim 2, wherein said tubular, carbon fiber reinforced plastic nail body includes carbon fibers which are disposed relative to one another so that said carbon fibers have a plurality of contacting locations at which said carbon fibers are interconnected.

4. A marrow nail as defined in claim 1, wherein said nail body includes an outer portion composed of plastic surrounding carbon fibers which are disposed in a tubular shape, said plastic being a biocompatible matrix material in which said carbon fibers are embedded and which is preferably of a composition which hardens at a temperature of approximately 380° C.

5. A marrow nail as defined in claim 1, wherein said marrow nail body has a generally C-shaped curvature along its longitudinal length.

6. A marrow nail as defined in claim 1, further comprising a marrow nail head disposed at an end of said nail body opposite said tip of said nail body, said marrow nail head comprising a metal element embedded therein.

7. A marrow nail as defined in claim 6, wherein said metal element comprises a hollow cylinder coaxially disposed inside said nail body, said metal element being hollow and having an inner wall which has a rough surface.

8. A marrow nail as defined in claim 7, wherein said rough surface is formed by a plurality of radial grooves.

9. A marrow nail as defined in claim 6, wherein said metal element is composed of titanium.

10. A marrow nail as defined in claim 1, wherein said tip of said nail body has an external diameter of approximately 10 millimeters.

11. A marrow nail as defined in claim 1, wherein said marrow nail body has a generally J-shaped curvature along its longitudinal length.

12. A marrow nail as defined in claim 7, wherein said inner wall having said rough surface is formed by a plurality of generally circumferentially disposed thread-shaped grooves.

* * * * *